US008428965B2

(12) United States Patent
Mojon Ojea et al.

(10) Patent No.: US 8,428,965 B2
(45) Date of Patent: Apr. 23, 2013

(54) SYSTEM FOR CLINICAL RESEARCH AND CLINICAL MANAGEMENT OF CARDIOVASCULAR RISK USING AMBULATORY BLOOD PRESSURE MONITORING AND ACTIGRAPHY

(75) Inventors: Artemio Mojon Ojea, Vigo (ES); Ramon Hermida Dominguez, Vigo (ES); Jose Ramon Fernandez Bernardez, Vigo (ES)

(73) Assignee: Universidade De Vigo, Vigo (ES)

( * ) Notice: Subject to any disclaimer, the term of this patent is extended or adjusted under 35 U.S.C. 154(b) by 94 days.

(21) Appl. No.: 12/850,623

(22) Filed: Aug. 4, 2010

(65) Prior Publication Data
US 2011/0035233 A1     Feb. 10, 2011

Related U.S. Application Data

(60) Provisional application No. 61/231,518, filed on Aug. 5, 2009.

(51) Int. Cl.
*G06Q 10/00* (2006.01)
*G06Q 50/00* (2012.01)

(52) U.S. Cl.
USPC ........................................... 705/2; 705/3

(58) Field of Classification Search ............ 705/2–3; 600/485, 490
See application file for complete search history.

(56) References Cited

U.S. PATENT DOCUMENTS

| 5,007,429 | A  | * | 4/1991  | Treatch et al. ................ 600/490 |
| 7,853,456 | B2 | * | 12/2010 | Soto et al. ......................... 705/2 |
| 2007/0244721 | A1 | | 10/2007 | Sackner-Bernstein et al. |
| 2008/0234587 | A1 | | 9/2008  | Bagha et al. |
| 2009/0192392 | A1 | * | 7/2009  | Riobo Aboy .................. 600/485 |

* cited by examiner

*Primary Examiner* — Michelle Le
(74) *Attorney, Agent, or Firm* — Mateo Aboy; Aboy & Associates PC

(57) ABSTRACT

Disclosed embodiments include a web-enabled system especially adapted for clinical research and clinical management of cardiovascular risk using ambulatory blood pressure monitoring (ABPM) data, actigraphy data, and clinical data. According to a disclosed embodiment the web-enabled system comprises (a) a web-enabled graphical user interface to enable a user to securely authenticate, securely upload clinical data, and navigate through a plurality of software modules; (b) a database to store user profiles, protocols, clinical data, ambulatory blood pressure monitoring (ABPM) recordings, actigraphy recordings, research data, and study results; and (c) a plurality of statistical methods and analysis techniques especially designed to automatically analyze the clinical cardiovascular risk data, and create customized reports of the results designed to assess cardiovascular risk based on ABPM and actigraphy.

11 Claims, 14 Drawing Sheets

800 Risk factors and diabetes mellitus

| | No | Yes | Year of diagnosis |
|---|---|---|---|
| Family history of premature CV disease<br>M at age < 55; W at age < 65 years | ○ | ○ | ✗ |
| Hypertension | ○ | ○ | |
| Diabetes mellitus<br>Fasting plasma glucose ≥ 7.0 mmol/l (126 mg/dl)<br>Postload plasma glucose > 11.0 mmol/l (198 mg/dl) | ○ | ○ | |

802 Subclinical organ damage

| | No | Yes |
|---|---|---|
| Left ventricular hypertrophy<br>electrocardiogram: Sokolow-Lyon > 38 mm; Cornell > 2440 mm·ms ; echocardiogram: LVMI M ≥ 125 g/m², W ≥ 110 g/m² | ○ | ○ |
| Carotid wall thickening (IMT > 0.9 mm) or plaque | ○ | ○ |
| Carotid-femoral pulse wave velocity > 12 m/s | ○ | ○ |
| Ankle/brachial BP index < 0.9 | ○ | ○ |

804 Established CV or renal disease

| | No | Yes | Date of diagnosis |
|---|---|---|---|
| Ischaemic stroke | ○ | ○ | |
| Cerebral haemorrhage | ○ | ○ | |
| Transient ischaemic attack | ○ | ○ | |
| Myocardial infarction | ○ | ○ | |
| Angina pectoris | ○ | ○ | |
| Coronary revascularization | ○ | ○ | |
| Congestive heart failure | ○ | ○ | |
| Diabetic nephropathy | ○ | ○ | |
| Renal impairment<br>serum creatinine M > 133 μmol/l (1.5 mg/dl), W > 124 μmol/l (1.4 mg/dl) | ○ | ○ | |
| Proteinuria<br>>300 mg/24 h | ○ | ○ | |
| Peripheral artery disease | ○ | ○ | |
| Advanced retinopathy<br>haemorrhages or exudates, papilloedema | ○ | ○ | |

806 Other diseases

If the patient currently has or had in the past any other disease of interest, please indicate the disease and the year of diagnosis:

FIG. 8

900 — Treatment adherence *(Morisky-Green test)*

| | No | Yes |
|---|---|---|
| Have you ever forgotten to take your medicine? | ○ No | ○ Yes |
| Are you sometimes neglectful in regard to your medicine hours? | ○ No | ○ Yes |
| Do you skip your medicine hours when you are feeling well? | ○ No | ○ Yes |
| When you feel badly due to the medicine, do you skip it? | ○ No | ○ Yes |

902 — Secondary effects (of antihypertensive medication)

The patient refers secondary effects: ○ No ○ Yes

904

| | No | Light | Moderate | Severe | | No | Light | Moderate | Severe |
|---|---|---|---|---|---|---|---|---|---|
| Abdominal pain | ○ | ○ | ○ | ○ | Fatigue | ○ | ○ | ○ | ○ |
| Angioedema | ○ | ○ | ○ | ○ | Blush | ○ | ○ | ○ | ○ |
| Bleeding | ○ | ○ | ○ | ○ | Headache | ○ | ○ | ○ | ○ |
| Cough | ○ | ○ | ○ | ○ | Nausea | ○ | ○ | ○ | ○ |
| Diarrhea | ○ | ○ | ○ | ○ | Palpitations | ○ | ○ | ○ | ○ |
| Dizziness or vertigo | ○ | ○ | ○ | ○ | Drowsiness | ○ | ○ | ○ | ○ |

Others (explain) 906

FIG. 9

Conventional clinic measurements

1000

| | Date of measurement (ex. 23/03/2008) | | Measurement device |
|---|---|---|---|
| | Hour (ex. 17:35) | | ○ Hg sphygmomanometer<br>○ Automatic oscillometric device<br>○ ABPM device |

| | First value | Second value | Third value | Average | Standing |
|---|---|---|---|---|---|
| Systolic BP (mmHg) | | | | | |
| Diastolic BP (mmHg) | | | | | |
| Heart rate (bpm) | | | | | |

1006

1004

ABPM measurement

1002

| Date when ABPM started (ex. 23/03/2008) | Time when ABPM started (ex. 17:35) | Assumed duration of ABPM<br>○ 24 hours  ○ 48 hours |
|---|---|---|

Rest-activity cycle

| First day | | Second day | | Third day |
|---|---|---|---|---|
| Bedtime | Awakening | Bedtime | Awakening | |
| : | : | : | : | |

1202 — Patient and series information

Gender and age
80.1-year-old female

Reason to perform ABPM
Resistant hypertension

Anthropometric data

| Height (cm) | Weight (kg) | BMI (kg/m²) | Body Surface Area (m²) | Waist perimeter (cm) | Cuff size |
|---|---|---|---|---|---|
| 155 | 73 | 30.4 Obesity class I | 1.72 | 96 Abdominal obesity* | Large |

Habits

| Cigarette smoking | Alcohol consumption | Physical activity |
|---|---|---|
| No | 0 units/week | Active |

1204 — Treatment before the study

Diagnosis of hypertension in 1998

Antihypertensive (more than 1 year ? attending the clinic with the medication taken)
- Doxazosina 2 mg   on awakening and at bedtime (two daily dose)
- Enalapril 20 mg   on awakening (a daily dose)
- Hidroclorotiazida 25 mg   on awakening

Other medication
- Statins   at bedtime

1206 — Conventional clinical blood pressure measurements (29/02/2008 — 08:30)

| | First value | Second value | Third value | Average | BP Stratification* | Standing |
|---|---|---|---|---|---|---|
| Systolic BP (mmHg) | 210 | 195 | 197 | 200.7 | Grade 3 hypertension | 178 |
| Diastolic BP (mmHg) | 70 | 75 | 72 | 72.3 | Isolated systolic hypertension | 80 |
| Pulse pressure (mmHg) | 140 | 120 | 125 | 128.3 | | 98 |
| Heart rate (bpm) | 61 | 59 | 58 | 59.3 | | 63 |

1208 — Analytical parameters (10/10/2007)

| Blood | | Urine | |
|---|---|---|---|
| HbA1 (%) | | Albuminuria (mg/24h) | 6.3 |
| Fasting glucose (mg/dl) | 93 | Albumin/creatinine ratio (mg/g) | |
| Total cholesterol (mg/dl) | 157 | | |
| Triglycerides (mg/dl) | 77 | | |
| HDL (mg/dl) | 61 | | |
| LDL (mg/dl) | 80.6 | | |
| Non-HDL cholesterol (mg/dl) | 96 | | |
| Creatinine (mg/dl) | 1.45 | | |
| Uric acid (mg/dl) | 7 | | |

Creatinine clearance (Cockroft-Gault equation; ml/min):   35.60
Creatinine clearance (body surface-adjusted Cockroft-Gault equations; ml/min per 1.73 m²):   35.75
Glomerular filtration rate (MDRD equation; ml/min per 1.73 m²):   36.92
   (moderate reduction in glomerular filtration rate — stage 3 chronic kidney disease)

1210 — Factors influencing prognosis*

Additional risk factors for cardiovascular disease
- Pulse pressure greater than 55 mmHg
- Age
- Abdominal obesity

Diabetes mellitus
No

Metabolic syndrome (ATP III definition, 2005)
Yes

Subclinical organ damage
- Left ventricular hypertrophy
- Low estimated glomerular filtration rate
- Low creatinine clearance

Established CV or renal disease
- Renal impairment (01/07/2006)
- Proteinuria (01/07/2006)

1212 — Cardiovascular risk stratification*

| | Normal BP | High-normal BP | Grade 1 hypertension | Grade 2 hypertension | Grade 3 hypertension |
|---|---|---|---|---|---|
| No other risk factor | Average risk | Average risk | Low added risk | Moderate added risk | High added risk |
| 1 or 2 risk factors | Low added risk | Low added risk | Moderate added risk | Moderate added risk | Very high added risk |
| 3 or more risk factors, subclinical organ damage, metabolic syndrome or diabetes | Moderate added risk | High added risk | High added risk | High added risk | Very high added risk |
| Established CV or renal disease | Very high added risk | Very high added risk | Very high added risk | Very high added risk | Very high added risk |

*European Society of Hypertension - European Society of Cardiology guidelines for management of arterial hypertension, 2007*

Proyecto Hygia. Bioengineering & Chronobiology Laboratories. University of Vigo

FIG. 12

SYSTEM FOR CLINICAL RESEARCH AND CLINICAL MANAGEMENT OF CARDIOVASCULAR RISK USING AMBULATORY BLOOD PRESSURE MONITORING AND ACTIGRAPHY

CROSS-REFERENCE TO RELATED APPLICATIONS

This application claims the benefit of U.S. Provisional Application No. 61/231,518 filed on Aug. 8, 2009 by the present inventors, which is incorporated herein by reference.

TECHNICAL FIELD

Disclosed embodiments relate to web-enabled systems for clinical research. Specifically, they relate to web-enabled systems for cardiovascular risk research and management.

BACKGROUND

Collaboration systems include any system which enables persons to share data, analyze data, upload data, and share results among a group of users. These systems are useful and a whole industry has emerged to develop and improve upon practical applications that take advantage of the connectivity these networks provide.

Currently, there is no disclosure available of any web-enabled system especially adapted for clinical research and clinical management of cardiovascular risk using ambulatory blood pressure monitoring (ABPM) and actigraphy. Software tools available with ABPM monitors and actigraphs are limited to standalone computers and are not designed to manage large clinical research studies and clinical trials. Furthermore, software tools and systems available do not include ABPM and synchronized actigraphy data management to support large scale research studies and do not include statistical techniques, ABPM indices, and ABPM/actigraphy specific methods to support the necessary research tasks to conduct cardiovascular risk studies and clinical trials.

SUMMARY

According to a disclosed embodiment the web-enabled system comprises: (a) a web-enabled graphical user interface to enable a user to securely authenticate, securely upload clinical data, and navigate through a plurality of software modules; (b) a database to store user profiles, protocols, clinical data, ambulatory blood pressure monitoring (ABPM) recordings, actigraphy recordings, research data, and study results; and (c) a plurality of statistical methods and analysis techniques especially designed to automatically analyze the clinical cardiovascular risk data, and create customized reports of the results designed to assess cardiovascular risk.

BRIEF DESCRIPTION OF THE DRAWINGS

FIG. 8 illustrates an embodiment of the form for retrieving data about personal and familiar history of cardiovascular risk factors.

FIG. 9 illustrates an embodiment of the GUI for obtaining information about treatment adherence and side effects.

FIG. 10 illustrates an embodiment of the GUI for collecting information about blood pressure measurements, taken both clinically and ambulatorily.

FIG. 12 illustrates an embodiment of the GUI showing a customized textual report for the individual analysis of a real patient.

DETAILED DESCRIPTION

Figure 1:
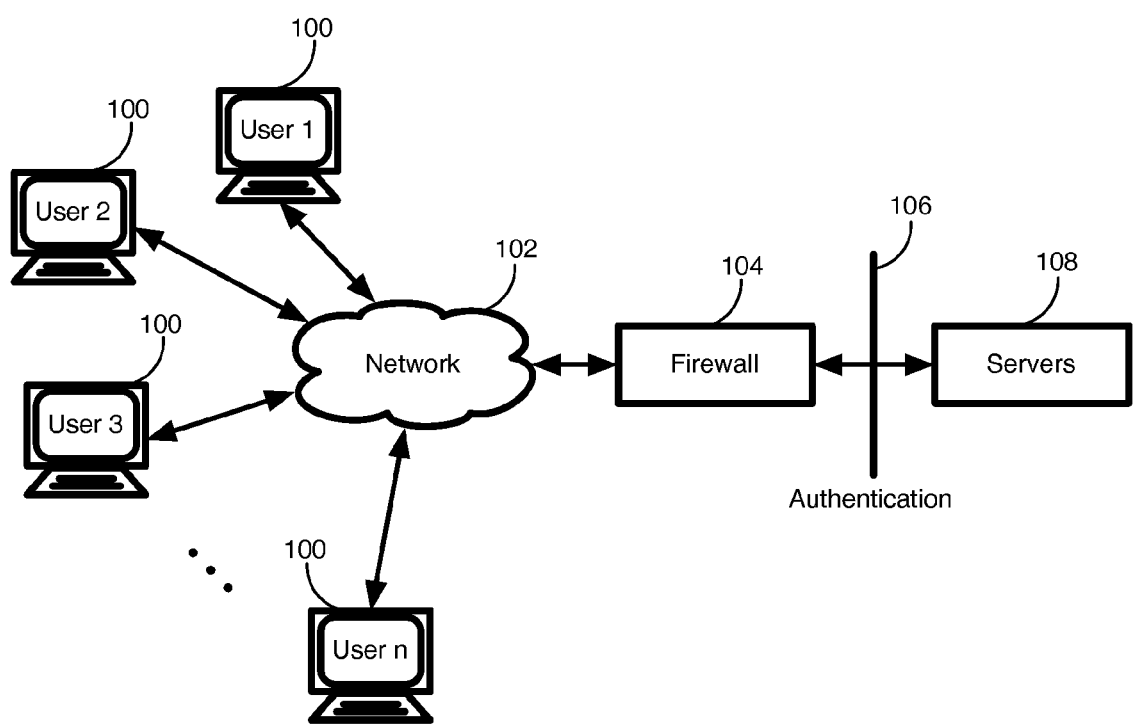
FIG. 1 illustrates a block diagram according to one embodiment.

Certain specific details are set forth in the following description and figures to provide a thorough understanding of various embodiments disclosed. Certain well-known details often associated with computing and software technology are not set forth in the following disclosure to avoid unnecessarily obscuring the various disclosed embodiments. Furthermore, those of ordinary skill in the relevant art will understand that they can practice other embodiments without one or more of the details described below. Aspects of the disclosed embodiments may be implemented in the general context of computer-executable instructions, such as program modules, being executed by a computer, computer server, or device containing a processor. Generally, program modules include routines, programs, objects, components, data structures, etc. that perform particular tasks or implement particular abstract data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that, given the description of the modules comprising the disclosed embodiments provided in this specification, it is a routine matter to provide working systems which will work on a variety of known and commonly available technologies capable of incorporating the features described herein.

A. System Architecture and Security According to Disclosed Embodiments

According to one embodiment, the system is created as one or more web servers that run an integrated online platform designed for cardiovascular risk research. It runs on a server computer that includes one or more processors and memory storage. The system supports encrypted data transfer through standard encryption protocols. A relational database such as MySQL is used to store user profiles, protocols, study data, study results, and collaboration team information. The system includes security modules, backups, and redundancy. All users are authenticated and the data is carefully controlled to ensure compliance with federal regulatory requirements such as the Health Information Portability and Accountability Act (HIPAA) and other information security laws. A particular embodiment is especially designed to comply with the LOPD information security standard, that is, the "Ley Orgánica 15/1999, de 13 de Diciembre, de protección de datos de carácter personal (LOPD)" (Spain) and substantially equivalent privacy and information security standards.

One of the disclosed embodiments comprises a web-enabled system especially adapted for clinical research and clinical management of cardiovascular risk using ambulatory blood pressure monitoring (ABPM) data, actigraphy data, and clinical data. The web-enabled system comprises (a) a web-enabled graphical user interface to enable a user to securely authenticate, securely upload clinical data, and navigate through a plurality of software modules; (b) a relational database to store user profiles, protocols, clinical data, ambulatory blood pressure monitoring (ABPM) recordings, actigraphy recordings, research data, and study results; and (c) a plurality of statistical methods and analysis techniques to automatically analyze said clinical data and said research data, and create customized reports of the results.

As shown in FIG. 1, a plurality of users 100 such as medical doctors, researchers, nurses, research coordinators, statisticians, and system administrators are connected to the system through a computer network 102 such as the Internet or an intranet. Each user has a specific set of permissions associated with their profile that gives them access to specific datasets, analysis methods, and study results. The servers receive and store the data 108 which is protected behind a firewall 104. Additionally, in order to grant access only to validated users and to maintain private the data from each user, the system includes a mechanism for secured authentication 106.

Figure 2:
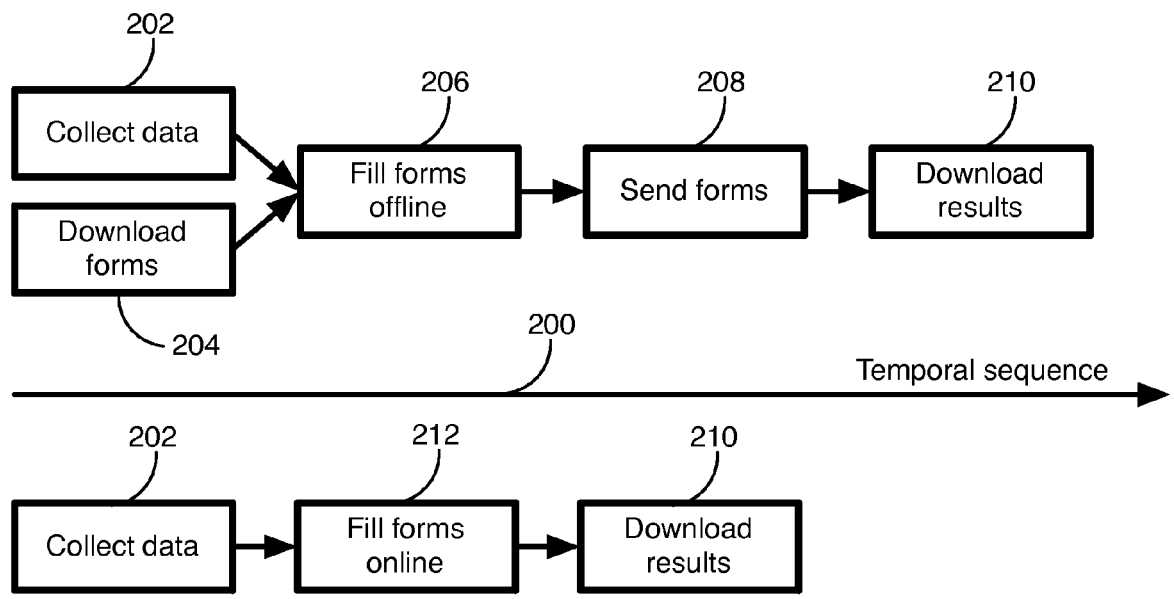
FIG. 2 illustrates two distinct options of data flux and temporal sequence of actions according to different embodiments.

FIG. 2 shows the temporal sequence of actions 200 that a user must follow in order to get the results from the system according to one embodiment. First, the user must collect locally all the needed data such as ABPM and actigraphy records, clinical history, medical history, and diary 202. Secondly, according to one embodiment, the user connects to the system and uploads the information 212 using any standard method to implement online forms such as PHP, ASP, Java, and substantially equivalent methods. Once these forms are filled and uploaded, the system automatically generates a plurality of statistical results 210 to automatically assess the cardiovascular risk of a particular subject. Alternatively, according to another embodiment, the completion of forms can be done offline using, for example, fillable PDF documents. This is particularly useful in situations where there is not a permanent connection to the network such as portable computers without an Internet connection. In this embodiment, the user has to download the forms 204 and fill them out offline 206. Once the forms are completed, the user connects to the network to upload the data contained in the fillable forms 208 and gets the results automatically 210. A limited number of users such as research directors or study coordinators have appropriate permissions to have access to analyze data of multiple subjects uploaded from multiple users and research centers in order to use the system to generate results for population studies.

Figure 3:
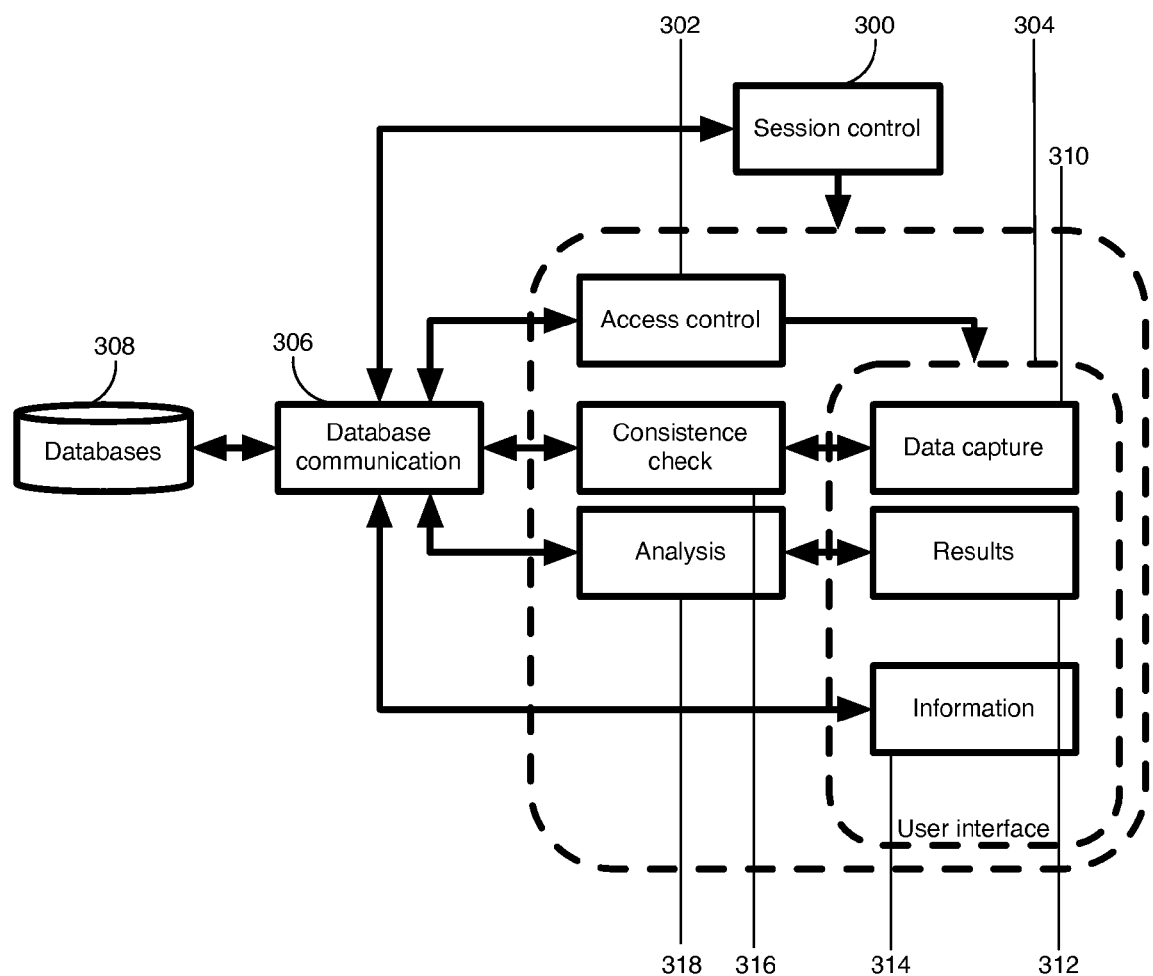
FIG. 3 illustrates an example of a system architecture according to one embodiment.

FIG. 3 illustrates an example of a system architecture according to one embodiment. In this embodiment, each user in the system has his own session. The module for session control 300 manages the authentication process 302, the user interface 304 and other modules of the system, allowing or disallowing the information exchange with the database communication module 306. The database communication module controls all the requests directed to databases 308. According to this embodiment, the user interface 304 includes, at least, a module for data input 310, a module for presenting results 312, and a module for accessing any other kind of non interactive information such as news, references, and downloadable forms 314. Modules to support research collaborations include forums, email, wikis, twikis, chats, audiovisual communication, and substantially equivalent online collaboration tools. All the collected data is checked 316 for completeness and consistency by the system (for example, the system checks that an antihypertensive treatment is not assigned to a patient declared as normortensive). When all the mandatory information is collected and stored, the session control module 300 launches the analysis process 318, which connects with the user interface to bring the results to the user.

Figure 4:
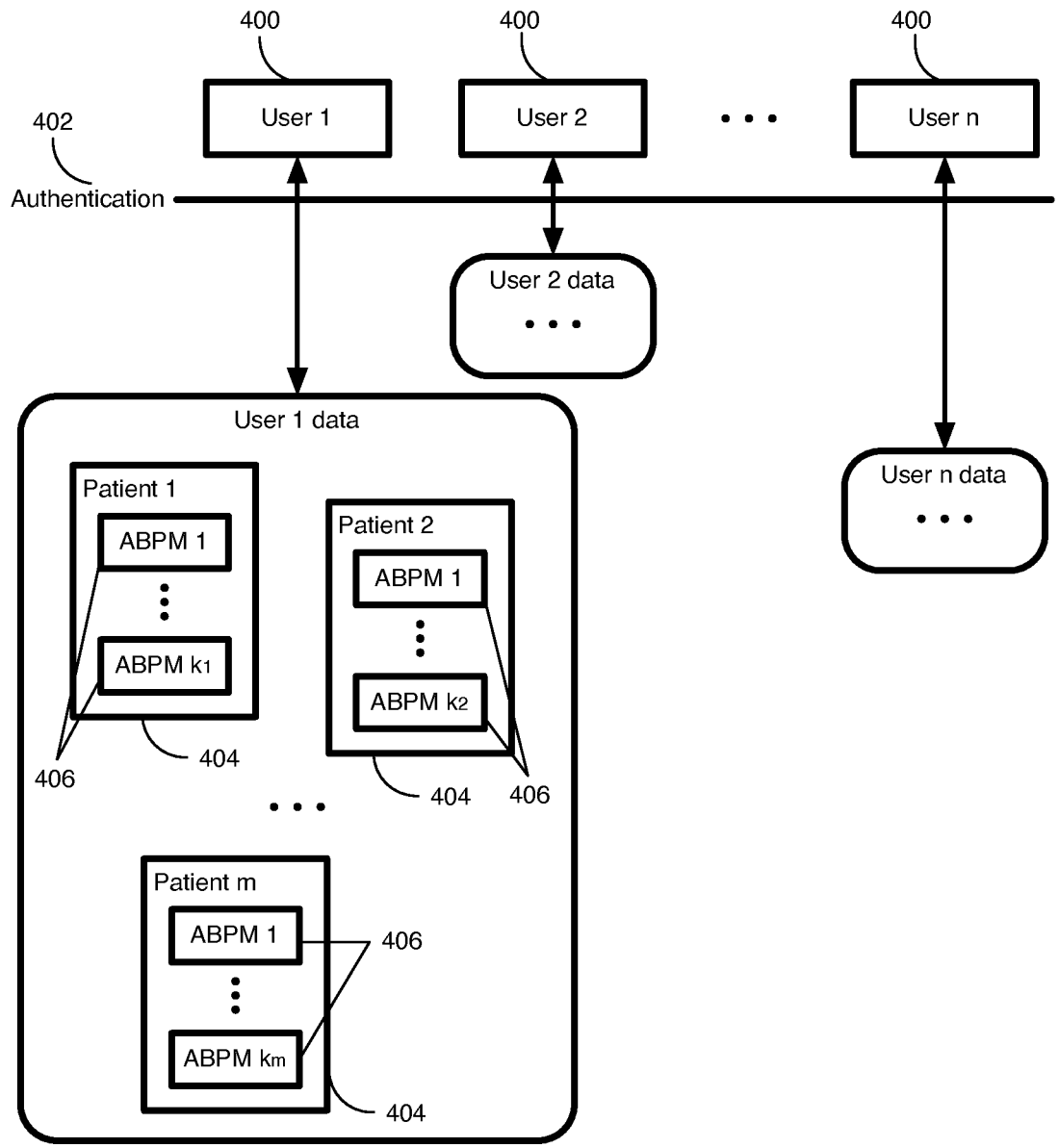
FIG. 4 illustrates the idea of personal data space for each user according to one embodiment.

According to a disclosed embodiment, the servers do not contain any data that could enable users or administrators to identify any singular patient. Moreover, information for each user is completely isolated from that of other users. This is represented in FIG. 4. When a user 400 attempts to access the system, he is required to authenticate himself 402. Once the access is granted, the user is only allowed to view and/or modify his own patients 404. Each patient may contain one or more ABPM records 406. According to an alternative embodiment, research directors may have permissions to use the system to analyze a plurality of patient files uploaded by a plurality of users from a plurality of research centers. Similarly, system administrators have access to all the parts of the system including methods, data, and settings.

B. Analysis of ABPM and Actigraphy Data According to Disclosed Embodiments.

Figure 5:
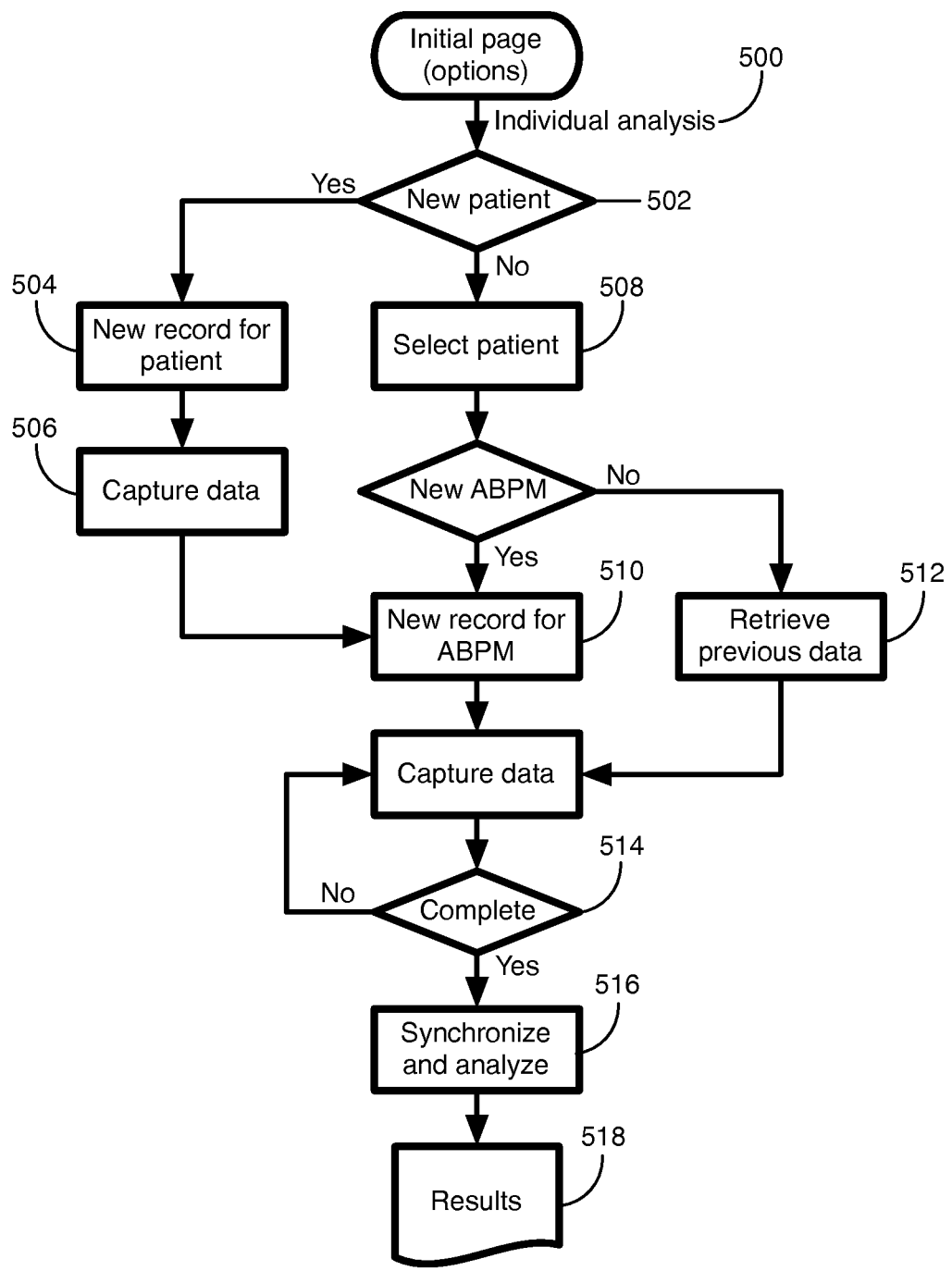
FIG. 5 illustrates the process of analyzing the data from an ABPM record according to one embodiment.
Figure 6:
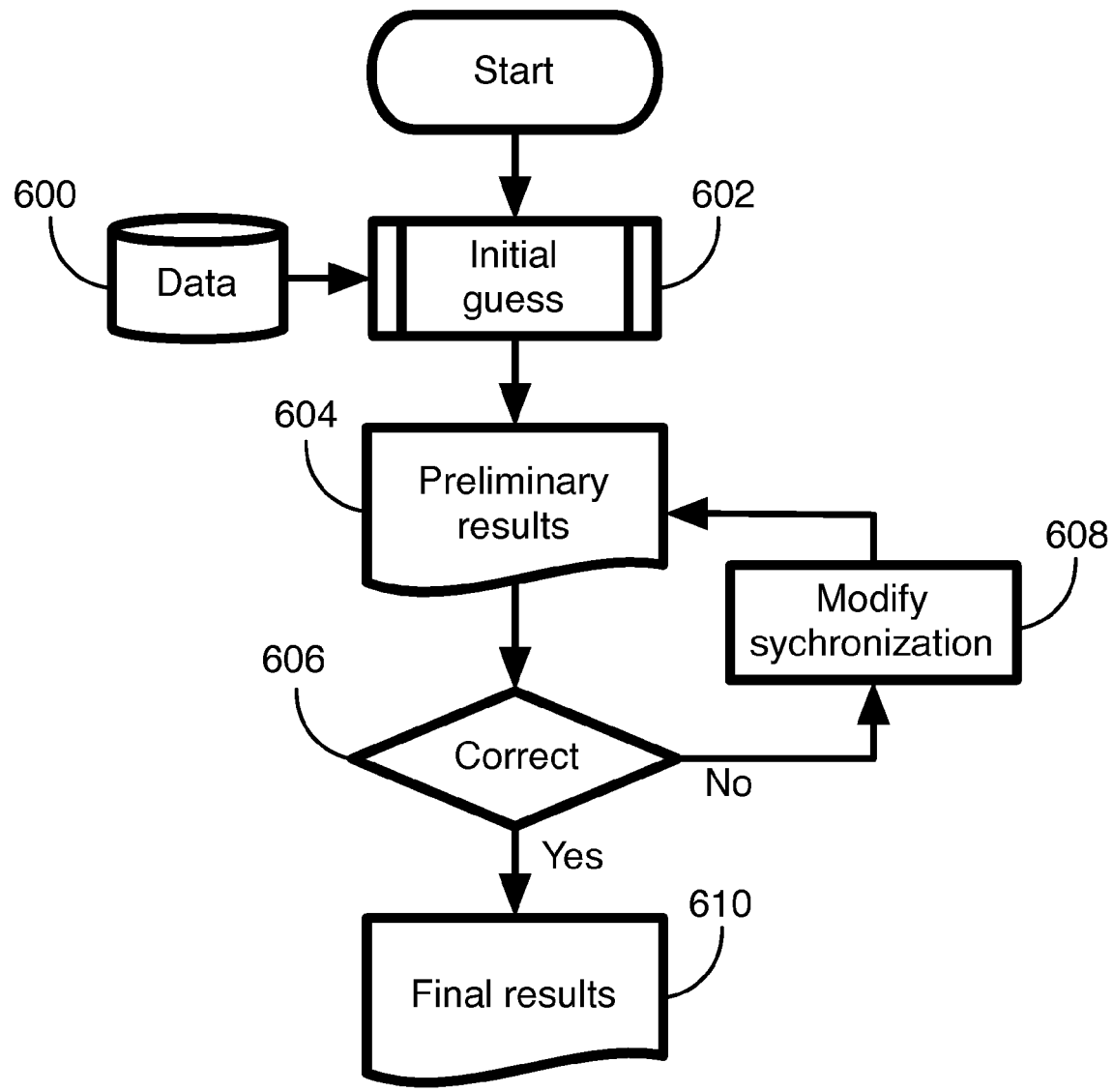
FIG. 6 illustrates the process of synchronizing blood pressure data with the sleep/awake cycle.

According to a disclosed embodiment, the system includes capability to perform individual statistical analysis and graphical visualization of a single ABPM record 500. This is illustrated with the diagram of FIG. 5. In this kind of analysis, the user must indicate 502 whether or not the data applies to a new patient or to a previous one. If the election was "new patient", a new record for this patient's data 504 is created in the database and is filled with the information provided by the user 506. If the desired analysis corresponds to a previous patient, the user is prompted for patient selection 508. Then, the user may want to add a new ABPM 510 or complete the data of a previous one 512. All the typed parameters 514 are checked for consistency and completeness prior to including them in the database and using them for analysis. Once all the data has been filed, in order to obtain accurate results, the blood pressure records must be synchronized based on the sleep/awake cycle 516. This automatic or semi-automatic procedure is illustrated in FIG. 6. After all the analyses are performed, the user is provided with the results 518 in the form of a plurality of descriptive statistical results, a plurality of inferential statistical results, and a plurality of graphical results to characterize the ABPM records. The process can be stopped at any point and the user will be redirected to the initial page. All the data introduced remains stored in the database for future completion 510.

C. ABPM Synchronization Based on Diaries or Actigraphy Data.

The system includes a module to perform synchronization of the blood pressure data according to the asleep/awake cycle. The final value of many of the ABPM derived parameters depends on the definition of "activity/rest", "day/night", "awake/asleep" or any similar terms. According to a disclosed embodiment, the synchronization process FIG. 6 starts by retrieving stored data 600. Then, based on diary information and/or actighraphy, for example, the system gives the user an initial guess about blood pressure synchronization 602. After the first analysis, the user is provided with a draft version of the results 604 in order to decide whether or not the analysis is correct 606. If the answer is "yes", the final reports are created 610 and the process ends. On the contrary, if the answer is "no", the user can adjust manually the synchronization parameters and analyze the data again 608.

D. Analysis of Pre-Treatment and Post-Treament ABPM and Actigraphy Data.

Figure 7:
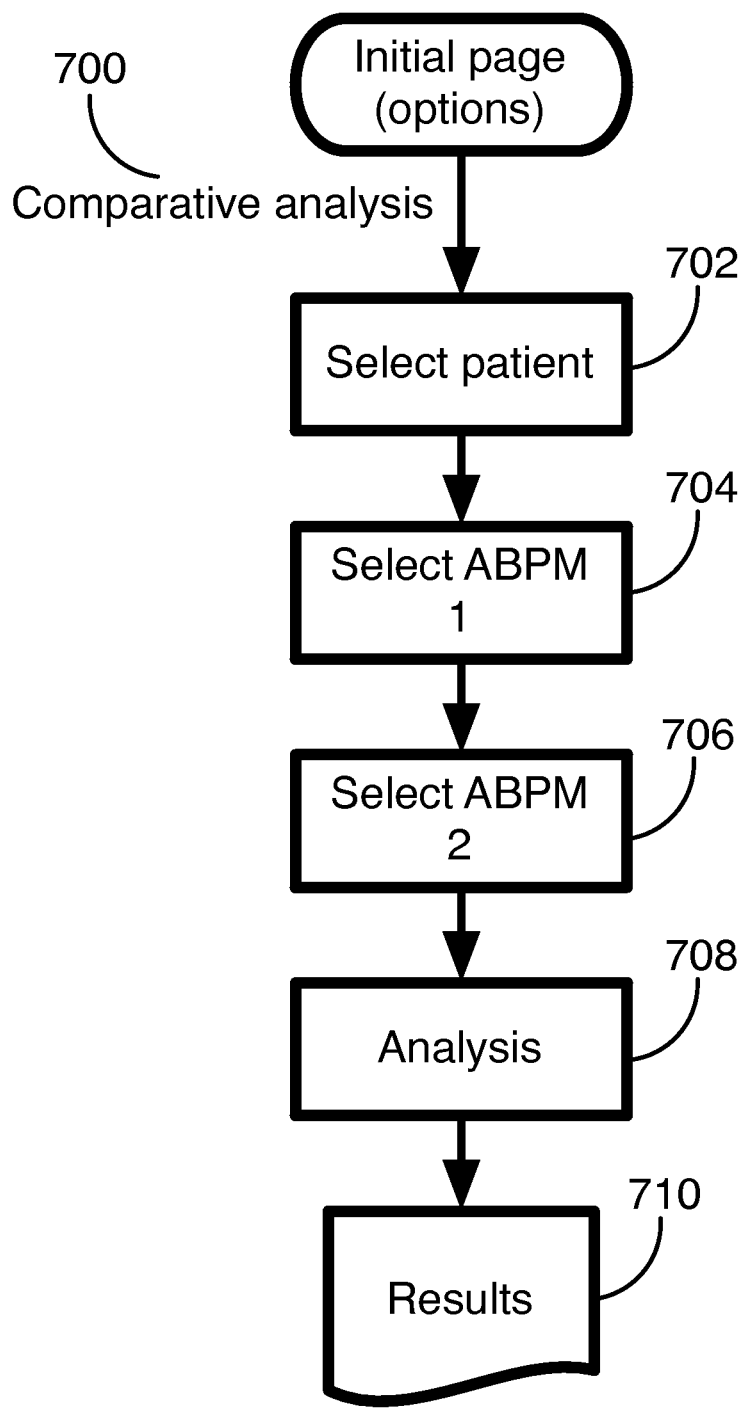
FIG. 7 illustrates the process of comparing the data from two ABPM records according to one embodiment.

According to a disclosed embodiment, the system includes a module to compare two or more ABPM records 700 in order to evaluate the effects of a new treatment, for example. The flow diagram to compare two series from the same patient is illustrated in FIG. 7. In this kind of analysis, the user must select the patient from those in database with two or more stored records 702. Then, the system shows the list of corresponding ABPM series in order to select two of them to be compared 704, 706. After that, the system retrieves all the necessary data and carries out the computations 708. Prior to conducting the analysis of a plurality of ABPM records, these records are automatically synchronized (according to the awake or asleep time, for instance) in order to avoid statistical significant blood pressure reductions due simply to different activity levels. Finally, the results 710 are reported using a customized report. Analysis of a plurality of ABPM records includes the analysis of pretreatment and post-treatment ABPM in order to determine the effects, efficacy, reduction, homogeneity, and duration of action of antihypertensive therapies, as well as the statistical significance of these parameters using parametric, nonparametric and/or computer intensive resampling methods such as bootstrap.

E. Data Collection and Associated GUIs According to Disclosed Embodiments.

FIG. 8 illustrates an embodiment of the GUI for collecting information about many factors that may influence the prognosis of the patient. In this embodiment, the form is built following the joint guidelines from the European Society of Hypertension (ESH) and the European Society of Cardiology (ESC), published in 2007. The system includes a plurality of guidelines and means for updating the guidelines to the current standard. The fields are grouped in four parts: the first section 800 records the information about familiar antecedents of cardiovascular disease, and previous diagnosis of hypertension and/or diabetes mellitus. The second section 802 collects information about conditions that, although not considered as established pathological disorders, are markers of organ damage. The third section 804 is designed for obtainining data of previous cardiovascular or renal events. Any other disease of interest not included in any previous section can be described in the last section 806. In this embodiment, the system is designed to make extensive use of radio buttons, menus, lists, and some other common elements of a modern GUI design in order to avoid mistakes whenever possible. The system includes a plurality of error checking methods.

As another example of one embodiment of the data entry booklet, FIG. 9 shows the fields to register "Treatment adherence" 900, the Morisky-Green test, and "Secondary effects" (Side Effects) 902. In this case, if the patient reports any side effect, the user must select the degree of the symptoms 904 from a list of the most common ones. Any other case must be explicitly explained 906.

FIG. 10 illustrates an embodiment of the GUI for collecting information about blood pressure measurements. The first part, "Conventional clinic measurements" 1000, enables the system to give results following the recommendations from the more common guidelines of clinical practice (such as JNC, ESH-ESC), based on casual measurement of blood pressure. This module requires that three sitting measurements of systolic and diastolic blood pressure and heart rate 1004 be serially taken (averages 1006, the results are automatically computed by the system and showed to the user). In the second part of FIG. 10, "ABPM measurement" 1002, the system requires the user to enter values that could be extracted directly from the ABPM and/or actigraphy records. These fields are used to check the uploaded ABPM and actigraphy files and detect possible errors in them.

E. Results Reported and Customized Reports According to Disclosed Embodiments.

Figure 11:
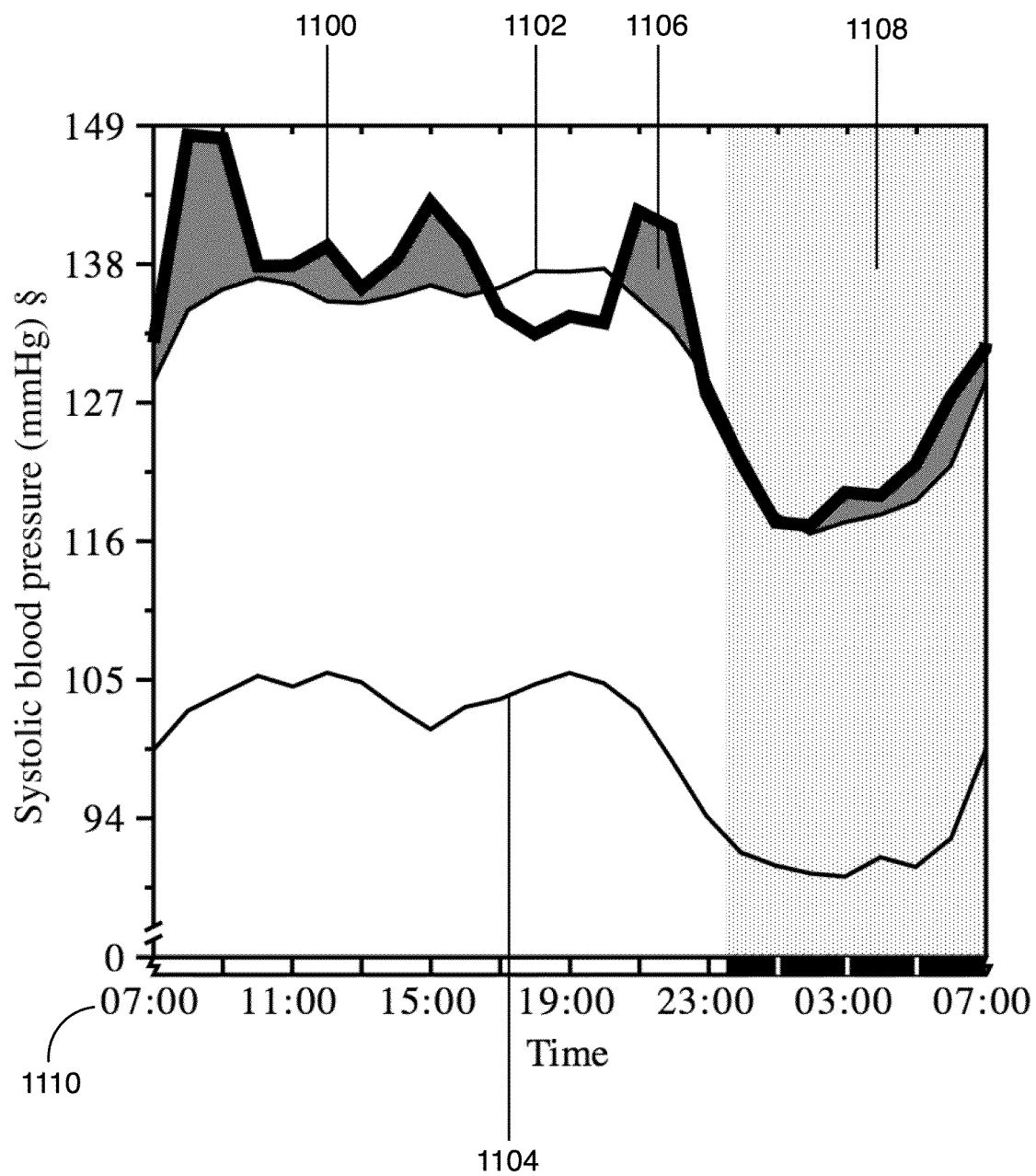
FIG. 11 illustrates a particular example of graphical output.

According to one embodiment, results are both textually and graphically presented. FIG. 11 illustrates an example of a graphical output of one of the analysis plots for systolic blood pressure. The system automatically calculates the Hyperbaric index 1106 which is defined as the area between the upper reference limit 1102 and the desired variable 1100, computed only where this is above the limit. Similarly, it includes a hypobaric index defined as the area of the region where the analyzed variable is below the lower tolerance limit 1104. In this embodiment, most of the parameters are computed for the awake and asleep 1108 periods separately and for the entire day also. Moreover, the graphical output is synchronized with the particular awake/asleep cycle of each patient. In the example, time axis 1110 begins at 07:00 because the patient became awake at that moment. In any other case, time axis will be shifted adequately. Analogously, the duration of the asleep period 1108 will be precisely adjusted for each ABPM record.

FIG. 12 illustrates an embodiment of the GUI showing a customized textual report for the individual analysis of a real patient. At the top of the sheet there is the identification of the analyzed series 1200. Below 1202 the system presents a brief summary of some basic facts about the patient and automatically classifies him according to parameters such as body mass index or abdominal obesity, taken into account factors such as age or sex. After that, 1204, the system outlines the treatment received by the patient prior to the ABPM. Moreover, 1206, the report shows the results of the conventional blood pressure measurements taken at the physician office and stratifies the blood pressure level according to the most common used guidelines of clinical practice. Below that 1208, the system presents the analytical parameters previously collected, and also derives others of clinical significance, such as non-HDL cholesterol, creatinine clearance and glomerular filtration rate. Furthermore, the report summarizes, as recommended by the 2007 joint guidelines from the European Society of Hypertension (ESH) and the European Society of Cardiology (ESC), all the factors that may influence the prognosis of cardiovascular disease 1210, including some conditions, such as the metabolic syndrome, that must be identified combining several particular facts. At the bottom of the report 1212, this embodiment illustrates the cardiovascular risk stratification following the previously cited guidelines. The system automatically remarks the particular risk level achieved for each patient.

F. Cardiovascular Risk Data Included According to Disclosed Embodiments.

According to one embodiment, the system is especially designed to securely store a plurality of cardiovascular risk clinical data for further processing, including ABPM, actigraphy, demographic data and patient habits, patient medical history, analytical data including bio-chemical parameters, office blood pressure data, drug therapy data. The automatic analysis conducted by the system includes statistical analysis of data collected by ABPM holters such as Systolic Blood Pressure (SBP), Mean Arterial Blood Pressure (MAP), Diastolic Blood Pressure (DBP) and Heart Rate (HR). Additionally, derived variables like Pulse Pressure (PP) and Double Product (DP) are automatically computed and analyzed, as well as the office blood pressure data, biochemical parameters, medical history, demographic and patient habits to generate a customized report.

G. Analysis Engine Module According to Disclosed Embodiments

According to one embodiment, the system analyzes the cardiovascular risk data available to a particular user to automatically create the desired customized cardiovascular risk analysis reports.

Specific indices that are part of the system and reported include the means of awake and asleep periods and the awake/asleep ratio, the global mean, the hyperbaric index and the percent of time of elevation, the hypobaric index and the percent of time of deficit, conventional descriptive statistics, a rhythmometric analysis, including estimations for rhythm-adjusted mean (MESOR), global amplitude, orthophase and bathyphase with their confidence intervals, the morning surge and the BP load, the Ambulatory Arterial Stiffness Index (AASI), TP ratio, smoothness index (SI), normalized smoothness index (SIn), and the reduction, duration and homogeneity index (RDH). The system includes the ability to calculate nonparametric confidence intervals based on bootstrap for the indices and ABPM metrics derived.

Figure 13:
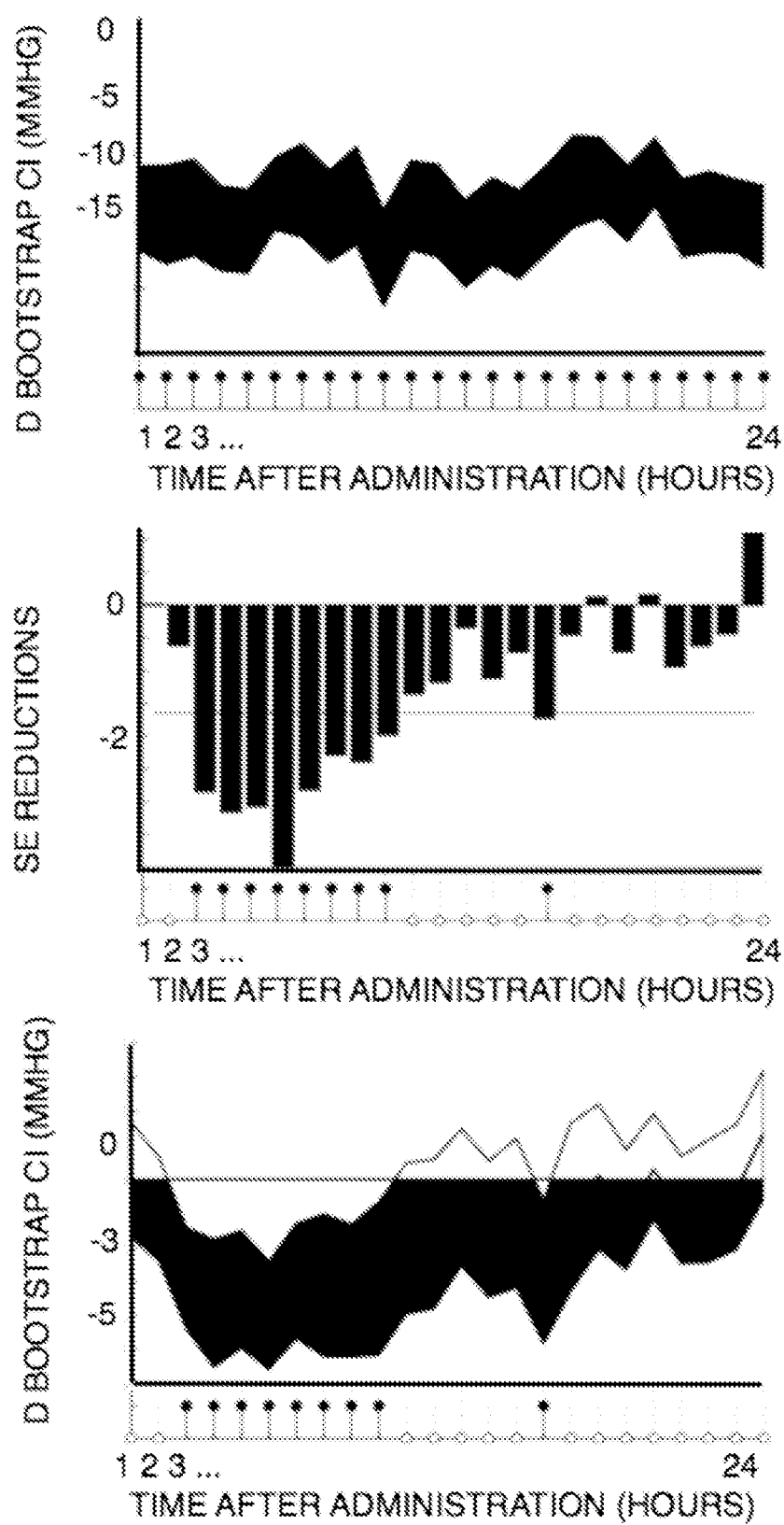
FIG. 13 illustrates an embodiment of analysis results automatically generated to display the results of the RDH index.
Figure 14:
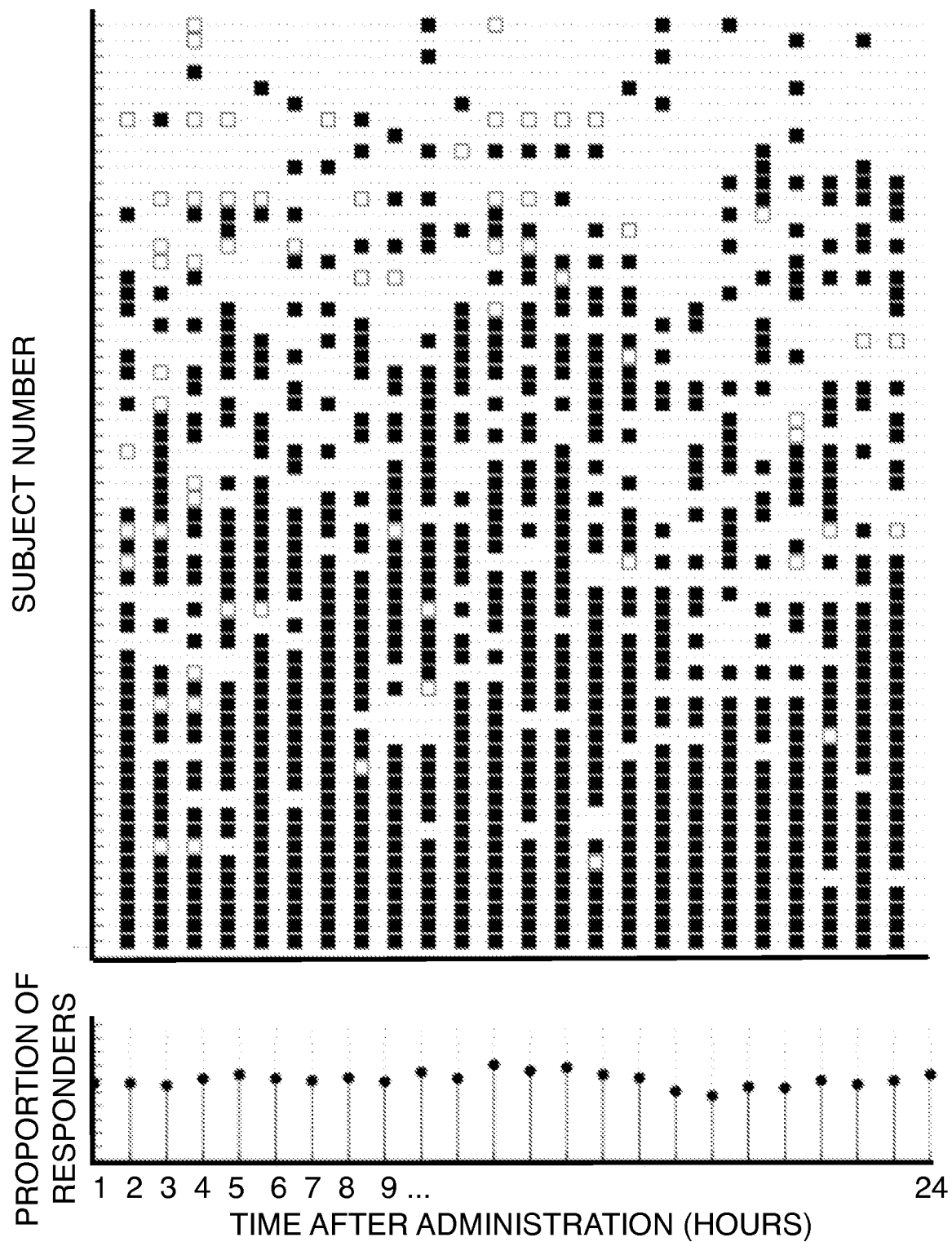
FIG. 14 illustrates an embodiment of analysis results automatically generated to display the results of the population RDH index.

FIG. 13 and FIG. 14 include sample graphs according to an embodiment of the customized report that includes the RDH index analysis for individuals and/or populations based on nonparametric computational statistics (e.g. bootstrap). According to this embodiment the system includes an implementation of the RDH method for evaluating antihypertensive treatment efficacy across patient populations. In accordance to one embodiment, the RDH is a population vector index and graphical method that provides the means for the statistical assessment of antihypertensive treatment reduction, duration, and homogeneity using synchronized ABPM by means of actigraphy. It is specifically designed as a tool to evaluate and compare blood pressure (BP) coverage offered by antihypertensive drugs over 24 h in populations. In accordance to one embodiment, the population RDH is a three-component vector index that incorporates information about the reduction, duration, and homogeneity of antihypertensive treatment, as well as their statistical significance over the 24 h period by quantifying: 1) the total number of hour-by-hour statistical significant BP reductions, 2) the maximum number of consecutive statistical significant reductions, and 3) the maximum number of consecutive non-significant reductions over the 24 hours, respectively, and reports two population graphs that characterize the effect of the treatment. The output of the RDH index can be used in clinical trials to characterize the effects of antihypertensive medications, and in clinical practice to guide antihypertensive treatment. FIG. 14 shows an example of a custom plot provided as part of the automatically generated customized report. This plot includes statistically significant blood pressure reduction results for each subject, the proportion of responders, and whether the reductions are statistically significant in the population under study.

Additionally, the system can be configured to report any index that is a function (i.e. a mathematical formula or algorithm) of ABPM, actigraphy and the data collected.

In order to study the longitudinal evolution of each patient, the system offers also the possibility of comparing two ABPM recordings of the same individual. This comparison includes studies of efficacy and homogeneity of antihypertensive treatment. The same kind of comparison can be obtained for selected populations.

H. Analysis Module with Novel Methods to Calculate the ABPM Statistics.

Hypertension diagnosis using ABPM is based on a plurality of statistics including the global mean over 24 hours, mean of the day blood pressure values, and mean of the night blood pressure values; as well as derived statistics such the mean reduction of blood pressure at night compared to day periods (or the decrease of asleep periods with respect to awake periods). According to one embodiment of the system the classical formula for calculating the mean, standard deviation, and standard error is implemented. According to an alternative embodiment, statistical parameters such as the mean, standard deviation, and standard error are calculated using novel methods designed to account for the fact that blood pressure measurements follow a non-uniform sampling scheme, that is, the time between measurements is not uniform (constant). ABPM monitors are typically configured to take measurements more often during the day (i.e. higher sampling frequency) than during the night (awake or activity versus asleep or rest). Additionally, ABPM monitors often fail to collect a given measurement due to artifact such as movement, and such measurement is attempted at a later time resulting in nonuniform sampling. Since ABPM monitors take more measurements during the expected awake period and blood pressure is higher during awake periods compared to rest periods, the global mean blood pressure (i.e. mean of all blood pressure measurements over 24 hours) is overestimated when using the classical method for calculating means. This results in false positives in the assessment and classification of patients according to their global blood pressure.

According to one embodiment the classical mean and standard error is calculated for all statistical measurements of ABPM, namely $$M = \bar{y} = \frac{1}{n}\sum_{j=1}^{n} y_j$$

$$se(M) = \frac{S}{\sqrt{n}}$$

$$S = \sqrt{\frac{\sum_{j=1}^{n}(y_j - M)^2}{n-1}}$$

where the ABPM data is composed of value pairs $(t_j, y_j)$ for $j=1, \ldots, n$; $t_j$ denotes the time instant where the blood pressure measurement $y_j$ takes place; $\bar{y}$ denotes the mean of all $y_i$ values; M is the global mean (also known as the 24 hour mean); and se(M) denotes the standard error of M.

According to another embodiment, the global mean M is calculated as a weighted mean of the activity periods and rest periods as follows:

$$M = \frac{L_d M_d + L_n M_n}{L_d + L_n} = \frac{L_d M_d + L_n M_n}{L}$$

where $M_d$ denotes the mean during the activity (asleep) period, $M_n$ denotes the mean during the rest (asleep) period, $L_d$ temporal length during the activity period, $L_n$ the temporal length during the rest period, and L denotes the total length of the ABPM record. In this embodiment the variance and standard error is calculated as follows:

$$\mathrm{Var}(M) = \frac{1}{L^2}\{L_d^2 \mathrm{Var}(M_d) + L_n^2 \mathrm{Var}(M_n)\}$$

$$\mathrm{Var}(M) = \frac{1}{L^2}\{L_d^2 se^2(M_d) + L_n^2 se^2(M_n)\}$$

$$se(M) = \sqrt{\mathrm{Var}(M)}$$

where $se^2(M_d)$ and $se^2(M_n)$ are the traditional standard error estimates of $M_d$ and $M_n$, respectively.

According to a third embodiment, the system employs a novel method for calculating means, variances, and standard errors in all the algorithms employed on the system which analyze ABPM data. According to this embodiment, the method is based on first calculating the ABPM mean for each hourly interval and then calculating the global mean as the mean of the hourly means. Consequently, it is a second order statistic. The global mean, the variance, and standard error are calculated as follows:

$$\sum_{i=1}^{C} k_i = n$$

$$\bar{y}_{i.} = \frac{1}{k_i}\sum_{j=1}^{k_i} y_{ij}$$

$$M = \bar{y}_{..} = \frac{1}{C}\sum_{i=1}^{C} \bar{y}_{i.}$$

where the original ABPM data $y_i$ is classified in C classes (for example, and without limitation, C=24); $y_{ij}$ denotes the j-th sample in class i with i=1, ..., C and j=1, ..., $k_i$, and $k_i$ is the number of ABPM samples in class i.

$$\mathrm{Var}(M) = \frac{\sigma_B^2}{C} + \frac{\sigma_W^2}{C^2}\sum_{i=1}^{C}\frac{1}{k_i}$$

where $\sigma_B^2$ denotes the variance among classes, and $\sigma_W^2$ is the variance within classes. Both of these variances are unknown in practical situations. In this embodiment they are estimated as follows, $$S_W^2 = \frac{1}{n-C}\sum_{i=1}^{C}\sum_{j=1}^{k_i}(y_{ij}-\bar{y}_{i.})^2$$

$$S_B^2 = \frac{1}{C-1}\sum_{i=1}^{C}k_i(\bar{y}_{i.}-\bar{y}_{..})^2$$

$$k' = \frac{1}{C-1}\left(n - \frac{\sum_{i=1}^{C}k_i^2}{n}\right)$$

$$\mathrm{Var}(M) = \frac{S_B^2 - S_W^2}{Ck'} + \frac{S_W^2}{C^2}\sum_{i=1}^{C}\frac{1}{k_i}$$

$$se(M) = \sqrt{\mathrm{Var}(M)}$$

The means and associated standard errors during activity periods and rest periods are calculated using the same equations with the appropriate samples. According to one embodiment, the activity and rest cycles are determined automatically by processing the accelerometer data.

According to a fourth embodiment, the means are calculated as the area A under the blood pressure curve divided by the temporal distance between the samples, that is, $$A = A_1 + A_2 + \ldots + A_{n-1}$$

$$A_i = \frac{y_i + y_{i+1}}{2}(t_{i+1} - t_i)$$

$$M = \frac{A_1 + \ldots + A_{n-1}}{L}$$

$$M = \frac{1}{2L}\{(t_2 - t_1)y_1 + (t_3 - t_1)y_2 + \ldots + (t_n - t_{n-2})y_{n-1} + (t_n - t_{n-1})y_n\}$$

$$\alpha_1 = \frac{t_2 - t_1}{2L},$$

$$\alpha_n = \frac{t_n - t_{n-1}}{2L},$$

$$\alpha_i = \frac{t_{i+1} - t_{i-1}}{2L},$$

$$i = 2, \ldots, n-1$$

$$M = \sum_{i=1}^{n}\alpha_i y_i$$

$$se(M) = \sqrt{\frac{\sum_{j=1}^{n}(y_j - \bar{y}^2)}{n-1}}\sqrt{\sum_{i=1}^{n}\alpha_i^2}$$

Other statistically derived ABPM parameters involving the mean, variance, standard deviation, and standard errors are calculated using one of these embodiments implemented in the system.

I. Cardiovascular Risk Management Recommendations According to Disclosed Embodiments For each analyzed subject the system provides a classification of: a) hypertension, b) dipper/non dipper, c) metabolic syndrome, d) renal function and e) increased cardiovascular risk according to approved guidelines of a scientific body (for example, and without limitation, the 2007 ESH/ESC guidelines). Furthermore, according to these guidelines, and using the collected information about the patient, the system may provide a therapeutic suggestion including non-pharmacological hygienic-dietetic recommendations, active principles, drug, dosage, and polytherapy regime. Moreover, taking into account the chronobiological results, that suggestion also includes an advice about the treatment time, administration-time-depedent considerations, and chronopharmacodynamics.

While particular embodiments have been described, it is understood that, after learning the teachings contained in this disclosure, modifications and generalizations will be apparent to those skilled in the art without departing from the spirit of the disclosed embodiments. It is noted that the foregoing examples have been provided merely for the purpose of explanation and are in no way to be construed as limiting. While the system has been described with reference to various embodiments, it is understood that the words which have been used herein are words of description and illustration, rather than words of limitations. Furthermore, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A system for clinical research and clinical management of cardiovascular risk implemented on a computer system with one or more processors and one or more storage elements, comprising:
   (a) a secure server running a web-enabled graphical user interface to enable a user to securely authenticate, securely upload clinical data, and securely navigate through a plurality of software modules;
   (b) a database to store in a memory storage device a plurality of user profiles, user permissions, protocols, cardiovascular risk clinical data, and study results;
   (c) a cardiovascular analysis module including a plurality of statistical methods and analysis techniques to automatically analyze said cardiovascular risk clinical data, and create customized reports of the results;
   (d) a blood pressure synchronization module configured for performing synchronization of ambulatory blood pressure data (ABPM) according to an asleep/awake cycle based on an actigraphy signal and pre-treatment and post-treatment ABPM; and
   (e) a module to compare two or more ABPM records from the same patient after performing said synchronization.

2. The system according to claim 1, wherein said cardiovascular risk clinical data comprises ambulatory blood pressure monitoring (ABPM) data from pre-treatment and post-treatment time periods employed to determine the effects of antihypertensive therapies after said ABPM data from said pre-treatment and said post-treatment time periods are synchronized by said blood pressure synchronization module in order to avoid erroneous statistically significant blood pressure reductions due to different activity levels.

3. The system according to claim 2, wherein said cardiovascular risk clinical data further comprises actigraphy data, and said actigraphy data is employed by said blood pressure synchronization module to perform said synchronization of ABPM data.

4. The system according to claim 3, wherein said cardiovascular module further includes analysis techniques employing a) demographic data and patient habits, b) patient medical history, c) analytical data including biochemical parameters, d) office blood pressure data, and e) drug therapy data.

5. The system according to claim 1, wherein said statistical methods and analysis techniques are configured for analyzing said cardiovascular risk clinical data resulting in a) hypertension diagnosis, b) assessment of antihypertensive therapies, c) evaluation and stratification of cardiovascular risk, d) classification of dipper status, e) detection of metabolic syndrome, and f) ABPM derived parameters.

6. The system according to claim 5, wherein said hypertension diagnosis comprises a plurality of methods based on ABPM and actigraphy data, said methods configured for calculating a plurality of metrics including a) 24-hour global mean and associated standard error, b) detection of awake and asleep period, c) awake and asleep periods means and associated standard errors, d) awake/asleep ratio, and e) dipper classification.

7. The system according to claim 5, wherein said ABPM derived parameters include hyperbaric index and percent of time of elevation, hypobaric index and percent of time of deficit, conventional descriptive statistics, a rhythmometric analysis comprising estimations of rhythm-adjusted mean (MESOR), global amplitude, orthophase and bathyphase with their confidence intervals, morning surge and BP load, and ambulatory arterial stiffness index (AASI).

8. The system according to claim 5, wherein said statistical methods and analysis techniques include methods of assessment of antihypertensive treatment reduction, duration, and homogeneity, treatment efficacy, and combinations thereof.

9. The system according to claim 8, wherein said methods for assessment of antihypertensive treatment reduction, duration, and homogeneity include TP ratio, smoothness index (SI), normalized smoothness index (SIn), and reduction-duration-homogeneity index (RDH) for individual subjects and research populations.

10. The system according to claim 8, further comprising means for analyzing and visualizing administration-time dependent effects and chronotherapy.

11. The system according to claim 6, wherein said means and associated standard errors are calculated based on first calculating an ABPM mean for each hourly interval and then calculating said global mean as a mean of the hourly means.

* * * * *